United States Patent [19]

Kawahara et al.

[11] Patent Number: 4,957,819
[45] Date of Patent: Sep. 18, 1990

[54] FRAMELESS AND CORELESS POROUS ENDOSSEOUS IMPLANT

[75] Inventors: Haruyuki Kawahara, Osaka; Seiichi Tsukamoto, Kanagawa; Yutaka Nomura, Kanagawa; Katsumi Tanaka, Kanagawa; Yasuyuki Ashiura, Kanagawa; Motonobu Yoshimura, Kanagawa, all of Japan

[73] Assignees: Haruyuki Kawahara, Osaka; Toho Titanium Co., Ltd., Tokyo, both of Japan

[21] Appl. No.: 358,828

[22] Filed: May 30, 1989

[30] Foreign Application Priority Data

Jun. 10, 1988 [JP] Japan .................. 63-144466

[51] Int. Cl.⁵ .................. G22F 3/00
[52] U.S. Cl. .................. 428/547; 419/2; 428/548; 428/550; 428/566; 428/610; 433/173
[58] Field of Search .................. 419/2; 428/547, 548, 428/550, 566, 610; 433/173

[56] References Cited

U.S. PATENT DOCUMENTS

| 2,267,918 | 12/1941 | Hildabolt | 428/547 |
| 2,464,517 | 3/1949 | Kurtz | 428/547 |
| 3,808,606 | 5/1974 | Tronzo | 433/173 |
| 3,905,777 | 9/1975 | Lacroix | 29/183.5 |
| 4,017,911 | 4/1977 | Kafeiiian et al. | 3/1.5 |
| 4,073,999 | 2/1978 | Bryan et al. | 428/311 |
| 4,156,943 | 6/1979 | Collier | 3/1.9 |
| 4,309,488 | 1/1982 | Heide et al. | 428/547 |
| 4,357,393 | 11/1982 | Tsuda et al. | 428/547 |
| 4,374,669 | 2/1983 | MacGregor | 75/208 R |
| 4,447,209 | 5/1984 | Sutter | 433/173 |
| 4,599,085 | 7/1986 | Riess et al. | 623/16 |
| 4,644,942 | 2/1987 | Sump | 623/16 |
| 4,671,768 | 6/1987 | Ton | 433/174 |
| 4,723,913 | 2/1988 | Bergman | 433/173 |
| 4,855,101 | 8/1989 | Mohs et al. | 419/8 |

Primary Examiner—Stephen J. Lechert, Jr.
Assistant Examiner—Leon Nigohosian
Attorney, Agent, or Firm—Koda & Androlia

[57] ABSTRACT

A frameless and coreless porous endosseous implant comprising a porous sintered metal layer (2) having a range of relatively large pores and porous sintered metal layers having a range of relatively small pores and laminated into one body by sintering integrally with the layer on either side thereof, or a porous singered metal layer having a range of relatively small pores and porous sintered metal layers having a range of relatively large pores and laminated into one body by sintering integrally with the layer on either side thereof, whereby the three layers each permit the ingrowth and penetration out of two or more kinds out of fibrous tissue, osteoid tissue and bone tissue in the pores thereof.

6 Claims, 1 Drawing Sheet

FRAMELESS AND CORELESS POROUS ENDOSSEOUS IMPLANT

BACKGROUND OF THE INVENTION

1. Field of the Invention

This invention relates to a porous endosseous implant made by sintering metal or alloyed metal powder and more particularly to a frameless and coreless porour endosseous implant made by integrally laminating a plurality of sintered metal layers by sintering.

2. Prior Art

Metal powder or alloyed metal powder (hereinafter only the metal powder is used as an example) harmless to the human body such as titanium, titanium alloy, etc. is pressed into powder moldings by metallurgical technology. An endosseous implant produced by the thus obtained powder moldings into one body has heretofore found its various forms of application in that a bone tissue, osteoid tissue and fibrous tissue each ingrow and penetrate into gaps between particles of various grain sizes (hereinafter referred to as pores) formed between powder particles and having various pore diameters and thereby attain a three-dimensional anchoring effect by a living body tissue to provide a good stability for an external force to the bone.

But the greatest disadvantage inherent in the prior art lies in the shortage of mechanical strength and especially when a sintered body is provided in a flat form, the body lacks in mechanical strength such as bending strength, shearing strength, impact strength, compression strength, so that a plate-shaped sintered body needs supporting by a reinforcing frame. Further, a columnar sintered body has been put into practical use in the form of composite construction wherein, for the similar purpose of reinforcement, a reinforcing core is passed through approximately the center of the sintered body (see Japanese patent application Nos. 260955/1986 and 277846/1987). In addition, in order to obtain the composite construction of the type described, the present applicant made also in his Japanese patent application No. 20788/1988 a technical proposal according to which the porous body and frame or core are firmly united and the body and frame or core are welded together not by sintering but by pressure welding as an advantageous means for obtaining the composite construction.

With the conventional type porous endosseous implant formed by sintering metal powder, the frame or core is essential for reinforcement, so that a certain degree of limitation has to be placed also in the reduction in the thickness and diameter of the implant member, which in turn imposes a limit on the range of application of the implant member.

In recent years, clinical reports on the implant have been made in a worldwide scale and various proposals as to the relation between the most effective implant and the bone tissue of living body have been made one after another. An up-to-date report on endosseous implants reveals that the amount of bone to remain with the implant after an insertion increases in proportion as the implant is smaller in thickness and that a degree of success in implant prosthetics is increased by leaving a bone tissue equal to or longer than the implant in thickness.

In this manner, it has proved highly desirable that the endosseous implant in itself be made as thin and strong as possible and be made of a material having the vigor to allow the bone tissue of a living body to ingrow into the porous implant.

An object of the invention is to provide an endosseous implant which meets the demand of the kind described.

SUMMARY OF THE INVENTION

A substantial means of solution provided by the invention for attaining the object described above is not to obtain a single porous sintered body of metal or alloy powder but to obtain a sintered laminated body formed of a plurality of porous sintered metal layers. The sintered body is produced in such a manner that distribution of powder particle size is changed with respect to the thickness of the sintered body of a desired size (mostly plate-shaped, cylindrical, and columnar bodies), namely, a pluarality of porous sintered metal layers each different in pore are laminated into one body by sintering at one operation and that one sintered metal layer having pore gaps adjusted to suit the ingrowth and penetration of bone tissue of a living body (bone tissue, osteoid tissue, and fibrous tissue) is reinforcedly supported in layers by another sintered metal layer having pores adjusted to be greater in strength than the former layer.

A detailed description will now be given of embodiments of the invention with reference to the accompanying drawing.

DETAILED DESCRIPTION OF THE INVENTION

Figure 1:
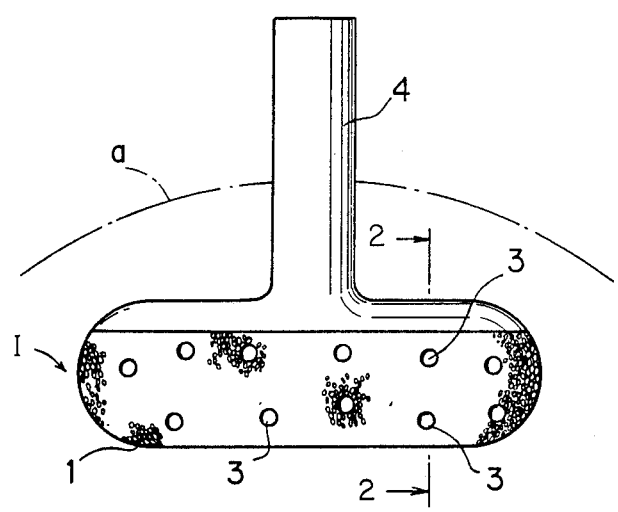
FIG. 1 is a front view of a plate-type embodiment of the endosseous implant of the invention used in a dental endosseous implant.

The invention relates to a frameless and coreless porous endosseous implant comprising a porous sintered metal layer 2 having a range of relatively large pores and porous sintered metal layers 1 and 1 each having a range of relatively small pores and laminated into one body by sintering integrally with the layer 2 on either side thereof, wherein the three layers 1, 2 and 1 permit the ingrowth therein and penetration therethrough of two or more kinds out of fibrous, osteoid and bone tissues and also relates to a frameless and coreless endosseous implant comprising a porous sintered metal layer 1 having a range of relatively small pores and porous sintered metal layers 2 and 2 each having a range of relatively large pores and being laminated into one body integrally with the layer 1 on both sides thereof, whereby the three layers 2, 1 and 2 permit ingrowth therein and penetration therethrough of two or more kinds out of fibrous, osteoid and bone tissues.

Out of the constructions described above, the invention defined in claim 1 is of such a type of construction wherein a soft fibrous tissue low in elastic modulus is allowed to essentially ingrow from each side of the implant and penetrate through the implant so as to softly respond to impact stress, for example, masticatory force. The invention in claim 2, in contrast to that in claim 1, is based on the premise of ingrowth and penetration of the osteoid and bone tissues higher in elastic modulus in order to mention than the fibrous tissue and is of such a type of construction which is enabled to cope with static stress. The mean range of pore gap of the porous sintered metal layer 1 is 50 μm or less and that of the layer 2 is 50 to 200 μm (if necessary, inclusive of a range wider than an average of 200 μm). Needless to say, since this is a range of pores concerning the ingrowth of the bone tissue of a living body, the critical range of pores does not form a restrictive boundary between the respective tissues and it is possible for different tissues to disorderly ingrow through the pores, so that the aforesaid range should be considered at least a reference. In some case, the layers 2 and 2 may be substantially the same in the range of pores and in other case they may be designed to be stepwise staggered in the range of pores. The same can be said of the case of using the layers 1 and 1. The pore gaps which completely permit the ingrowth and penetration of the bone tissue therein are up to the order of 1000 μm, so that when it is difficult to form the pores of the size exceeding this range, it is possible to form the pores by drilling the thickness of the implant by an electrobeam method, laser beam method, electrospark method, mechanical drilling method according to the Japanese patent application No. 264994/1985 which the present applicant filed separately, U.S. Pat. No. 931,660. British patent No. 8626646, West German patent application No. P3639030.5, and Italian patent application No. 22306A/86.

Viewed from the point of strength of the sintered body, a coarse powder sintered body is large in pores and relatively small in strength, while a fine powder sintered body is small in pores and large in strength. Porosity (porosity rate) of the sintered metal layers 1 and 2 together with the pores has bearing upon the ingrowth and penetration of the tissues and upon the strength of the layers 1 and 2. Higher porosity is more effective for ingrowth of more tissues, while it works reversely on strength. This point must also be considered when porosity is selected. Included under the metal or alloyed metals to be used are simple substance metals such as Ti, Zr and Ta, Ti alloy, Zr alloy, Ta alloy, Fe-Ni-Cr alloy, Co-Cr-Mo alloy and similar other materials harmless to the human body. It is possible to obtain a sintered metal layer having different pores formed therein by the use of the powder materials mentioned above by laminating pressure powder molding layers formed respectively of relatively fine powder and relatively coarse powder and sintering the resulting layers into one body in nonoxidizable atmosphere. If necessary, it is possible to obtain dimensional accuracy in the surface of the sintered metal layer by machining in subsequent to the lamination of the sintered metal layers into one integral body or reopen the pores in the surface by chemically etching the surface of the sintered metal layer having its pores crushed by the machining.

Relation between factors in adjusting the pores in the layers 1 and 2 and pore diameter is shown below:

| Pore size reduced | Factor | Pore size increased |
|---|---|---|
| Large | ← Forming pressure → | Small |
| Small | ← Powder size → | Large |
| High | ← Sintering pressure → | Low |
| Long | ← Sintering time → | Short |

Notwithstanding the fact that the implant is relatively thin in its entire thickness, the implant of the invention defined in claim 1 is enabled to be a frameless and coreless implant because of improvement of the whole implant in mechanical strength by relatively fine metal powder sintered layers 1 and 1 disposed on either side of the implant and relatively coarse metal powder sintered layer 2 interposed between the layers 1 and 1 and can softly cope with impact stress because a soft fibrous tissue ingrows substantially into the layers 1 and 1 and penetrates therethrough.

The implant defined in claim 2 permits the substantial ingrowth and penetration therein of osteoid and bone tissues through the pores in the relatively coarse metal powder sintered layers 2 and 2 on either side thereof and can sufficiently cope with static stress, although the support of the implant in claim 2 is not so soft as the one defined in claim 1. Because it is expected that the implant in this embodiment can be further increased in strength as a whole by the high mechanical strength provided by the sintered metal layers 2 and 2 on either side of the sintered metal layer interposed therebetween, not only the entire thickness of the implant can be further reduced but the fibrous tissue can also make ingrowth and penetration through the layer 1 and partially demonstrate its soft support, depending upon the manner in which the pores are formed in the layer 2.

EMBODIMENTS

EXAMPLE 1

Figure 2:
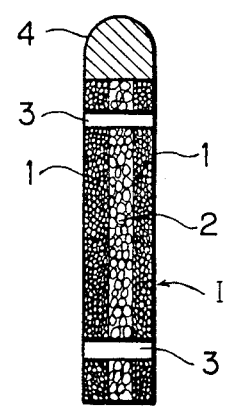
FIG. 2 is an enlarged sectional view taken along the line b—b of FIG. 1.

The embodiment shown in FIGS. 1 and 2 is an embodiment corresponding to claim 1 and shows a plate type endosseous implant to be embedded in an alveolar bone a, and an implant body 1 is connected by sintering, welding or pressure welding integrally to the lower part of a metal post 4 to be crowned with an artificial tooth (not shown). The implant body 1, as shown in FIG. 2, is formed of three layers. The three layers are laminated into one body in such manner that the layers 1 and 1 forming the right and wrong side surface of the implant body 1, respectively, have about 30% porosity and include relatively fine pores in the range of 30 to 50 μm in diameter and a sintered metal layer 2 having relatively large pores in the range of 50 to 200 μm is interposed between the layers 1 and 1, and the layers 1, 2 and 1 are laminated into one body by sintering.

In the embodiment, by the use of the idea disclosed in the previous Japanese patent application No. 264994/1985, the implant further provided at random with tubular channels 3 . . . to permit the bone tissue to penetrate the thickness of each layer by an electrobeam method, laser beam method, electrospark method or mechanical drilling method in order that the implant may have through-holes having a diameter in the range of 200 to 1000 μm to permit vigorous penetration of bone tissue into and through the sintered metal layers 1 and 1.

The reason for formation of tubular channels 3 . . . is to promote the penetration through the pores 3 which effectively supports the implant relative to static stress by forming pores in the range of 20 to 1000 μm in point of pore diameter, number and distribution over the area of the layers depending upon the case of disease, the pores being hard to form intentionally by the metal powder of the grain size to be later described.

The metal powder was used in such manner that fine pure titanium powder (50 to 100 μm) was used for the layers 1 and the powder (100 to 200 μm) was used for the layer 2. The three layers 1, 2 and 1 each were formed by pressure powder molding and were thereafter laminated into one body under the sintering conditions: $1 \times 10^{-4}$ Torr. in degree of vacuum, 100° C. in temperature, and 1 hour in treatment time, whereby the layers 1 and 1 having pores 30 to 50 μm large and a layer having pores 50 to 2000 μm large were obtained respectively. The implant body 1 formed of the thus obtained and a titanium alloy post 4 were subjected to argon arc welding by use of a titanium welding rod by placing the post 4 on the body 1 edge to edge via beveling.

EXAMPLE 2

Figure 4:
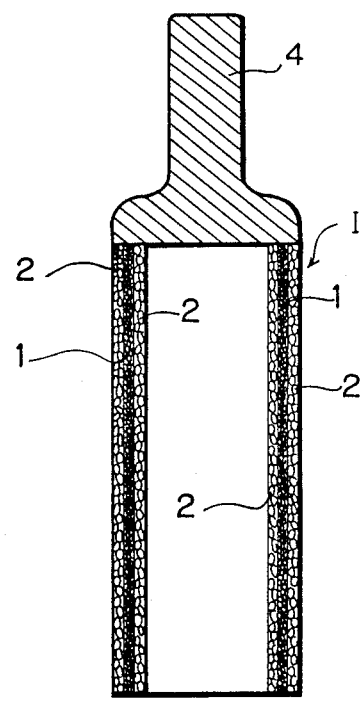
FIG. 4 is an enlarged sectional view taken along the line c—c of FIG. 3.
Figure 3:
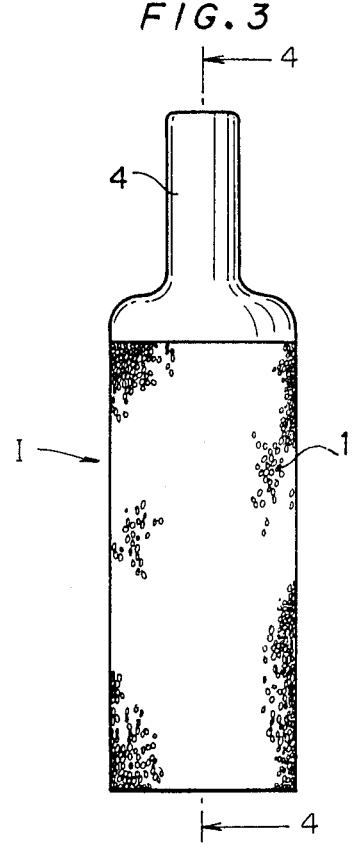
FIG. 3 is a front view of a cylindrical type embodiment of the dental endosseous implant.

The embodiment shown in FIGS. 3 and 4 is the one corresponding to claim 2 and shows the case wherein the embodiment is applied to a cylindrical type dental endosseous implant adapted to be screwed into the alveolar bone a. The embodiment is of such three layer construction in which the post 4 is welded integrally to the top of the implant body 1 formed cylindrical with the lower part left open by interposing the inner layer 1 between the layers 2 and 2 in order reverse to that in Example 1. Accordingly, the cylindrical implant is left hollow with no core inside. The layers 1 and 2 are entirely the same in material, production method and welding method as those of the first embodiment.

Incidentally, the post 4 is provided not for the purpose of reinforcing the implant body 1 but for the purpose of protecting a bone mucous membrane and cartilage tissue against possible inflammation and secondary infection caused by bacteria invading that portion of the porous implant projecting beyond the alveolar bone a through the multipores of the projecting portion.

In place of the plate type and cylinder type implants described above, the invention can find its application in a general submersible endosseous implant.

Because the implant of the invention defined in claim 1 permits mainly the fibrous tissue to make ingrowth and penetration through the sintered metal layer having a range of relatively fine pores therein, the implant is not only enabled to cope softly with impact stress but is also enabled to maintain necessary strength and to have high porosity on either side layer of the implant to permit ingrowth of a large amount of fibrous tissue irrespective of the implant body being coreless and frameless, because the implant body is reinforced in the direction of its thickness by the sintered metal layer in the middle of the implant body having a range of relatively coarse pores. Accordingly, the implant of the type described finds its optimum application in the dental field, orthopedic field and the like in which impact stress is imparted to an afteroperation implant. The implant claimed in claim 2 is mainly intended for ingrowth and penetration of osteoid and bone tissues, so that although different from the implant in claim 1 from the viewpoint of soft support relative to stress, yet resistance by hard tissue to stress is conversely produced, and consequently the implant is not only suitable for an implant based on static stress but further promotes reduction in the thickness of the implant by the increased strength given by the sintered metal layer on either outside of the implant.

Since both embodiments have, in addition to the grain size, forming pressure, sintering temperature, and sintering time to do with adjustment of the pores, not only the adjustment of the pores is easy but the employment of pressure powder molding technique and sintering technique as a production method also facilitates mass production. The invention provides excellent effects in this respect.

We claim:

1. A frameless and coreless porous endosseous implant comprising a porous sintered metal layer (2) having a range of relatively large pores and porous sintered metal layers (1) and (1) each having a range of relatively small pores and laminated into one body by sintering integrally with the layer (2) of relatively large pores on either side thereof, whereby said three layers (1), (2), and (1) each permit the ingrowth and penetration of two or more kinds of tissue selected from the group consisting of fibrous tissue, osteoid tissue and bone tissue in the pores thereof, said large pores having a mean size range of of 50-200 μm.

2. A frameless and coreless porous endosseous implant comprising a porous sintered metal layer (1) having a range of relatively small pores and porous sintered metal layers (2) and (2) each having a range of relatively large pores and laminated into one body by sintering integrally with the layer (1) on either side thereof, whereby said three layers (2), (1), and (2) each permit the ingrowth and penetration of two or more kinds of tissues selected from the group consisting of fibrous tissue, osteoid tissue and bone tissue in the pores thereof, said large pores having a mean size range of of 50-200 μm.

3. An endosseous implant according to claim 1 or 2 wherein the range of the porous sintered metal layer (1) having a range of relatively small pores is 50 μm or less on an average and the porosity of the layer is 30% or more on an average.

4. An endosseous implant according to claim 1 wherein coarse tubular channels 3 passing transversely through the respective thickness of the implant are formed in a desired range of distribution thereover.

5. An endosseous implant according to claim 4 wherein said tubular channels 3 are in the range of 200 to 1000 μm in diameter.

6. An endosseous implant according to claim 4 or 5 wherein said tubular channels (3) are formed by a method selected from the group consisting of electrobeam method, laser beam method, electrospark method and mechanical drilling method.

* * * * *